US005667971A

United States Patent [19]
Hochberg

[11] Patent Number: 5,667,971
[45] Date of Patent: Sep. 16, 1997

[54] METHOD FOR DETERMINING DNA SEQUENCES

[75] Inventor: Alan M. Hochberg, Hockessin, Del.

[73] Assignee: Dade Chemistry Systems Inc., Deerfield, Ill.

[21] Appl. No.: 473,383

[22] Filed: Jun. 7, 1995

Related U.S. Application Data

[63] Continuation of Ser. No. 961,212, Oct. 14, 1992, which is a continuation of Ser. No. 564,143, Aug. 7, 1990, abandoned.

[51] Int. Cl.$^6$ .............................. C12P 19/34; C12Q 1/68
[52] U.S. Cl. .............................. 435/6; 435/91.1; 935/77; 935/78
[58] Field of Search ..................... 435/6, 91.1; 935/77, 935/78

[56] References Cited

U.S. PATENT DOCUMENTS

| | | | |
|---|---|---|---|
| 4,811,218 | 3/1989 | Hunkapiller et al. | 364/413.01 |
| 5,124,247 | 6/1992 | Ansorge | 435/6 |

FOREIGN PATENT DOCUMENTS

| | | |
|---|---|---|
| 3839397 | 5/1990 | Germany. |
| 3841565 | 6/1990 | Germany. |

OTHER PUBLICATIONS

A. M. Maxam, et al., Meth. in Enzym, vol. 65, pp. 499–599 (1908).
F. Sanger, et al., Proc. Nat. Acad. Sci. USA, vol. 74, pp. 5463–5467 (1977).
S. Beck, Anal. Biochem, vol. 164 (2) pp. 514–520 (1987).
S. Beck, Nucleic Acids Res. vol. 17, pp. 5115–5123 (1989).
L. M. Smith, et al., Nucleic Acids Res., vol. 13, pp. 2399–2412 (1985).
W. Ansorge, et al., J. Biochem. Biophys. Meth., vol. 13, pp. 315–323 (1986).
H. Kambara, et al., Biotechnology, vol. 6, pp. 816–821 (1988).
Journal of Biochemical and Biophysical Methods, vol. 20, No. 1, 1989, Elsevier, Amsterdam pp. 47–52, W. Ansorge et al.: 'Automated Sanger DNA sequencing with one label in less than four lanes on gel', see the whole document.
BioTechnology, vol. 6, Jul. 1988, pp. 816–821, 'Optimization of parameters in a DNA sequenator using fluorescence detection', see the whole document.
Ansorge et al., Nuc. Acids Res. 15 (11):4593–4602 (Jun. 1987).

*Primary Examiner*—Stephanie W. Zitomer
*Attorney, Agent, or Firm*—Linda M. Buckley

[57] ABSTRACT

A method is disclosed for determining the sequence of DNA bases by using two electrophoretic lanes for each DNA sample to be sequenced. Each lane incorporates two dyes.

9 Claims, 4 Drawing Sheets

METHOD FOR DETERMINING DNA SEQUENCES

This is a continuation of application Ser. No. 07/961,212, filed Oct. 14, 1992, which is a continuation of application Ser. No. 07/564,143, filed Aug. 7, 1990, now abandoned.

CROSS REFERENCE TO RELATED PATENTS AND APPLICATIONS

This application is related to inventions described in U.S. Pat. No. 4,833,332 entitled "Scanning Fluorescent Detection Systems", issued to Robertson et al., to an application Ser. No. 07/057,566, filed Jun. 12, 1987 by Prober et al. entitled "Method, System, and Reagents for DNA Sequencing" (IP-597-A), and to an application Ser. No. 07/545,765, filed Jun. 29, 1990, by Dam et al. entitled "Method for Determining DNA Sequences" (IP-0846).

FIELD OF THE INVENTION

This invention relates to a method for obtaining more accurate DNA sequence information.

BACKGROUND OF THE INVENTION

DNA sequencing is one of the cornerstone analytical techniques of modern molecular biology. The development of reliable methods for sequencing has lead to great advances in the understanding of the organization of genetic information and has made possible the manipulations of genetic material (i.e., genetic engineering).

There are currently two general methods for sequencing DNA: the Maxam-Gilbert chemical degradation method [A. M. Maxam et al., *Meth. in Enzym.*, Vol. 65, 499–559 (1980)] and the Sanger dideoxy chain termination method [F. Sanger, et al., *Proc. Nat. Acad. Sci. USA*, Vol. 74, 5463–5467 (1977)]. A common feature of these two techniques is the generation of a set of DNA fragments which are analyzed by electrophoresis. The techniques differ in the methods used to prepare these fragments.

With the Maxam-Gilbert technique, DNA fragments are prepared through base-specific, chemical cleavage of the piece of DNA to be sequenced. The piece of DNA to be sequenced is first 5'-end-labeled with $^{32}P$ and then divided into four portions. Each portion is subjected to a different set of chemical treatments designed to cleave DNA at positions adjacent to a given base (or bases). The result is that all labeled fragments will have the same 5'-terminus as the original piece of DNA and will have 3'-termini defined by the positions of cleavage. This treatment is done under conditions which generate DNA fragments which are of convenient lengths for separation by gel electrophoresis.

With Sanger's technique, DNA fragments are produced through partial enzymatic copying (i.e., synthesis) of the piece of DNA to be sequenced. In the most common version, the piece of DNA to be sequenced is inserted, using standard techniques, into a "sequencing vector", a large, circular, single-stranded piece of DNA such as the bacteriophage M13. This becomes the template for the copying process. A short piece of DNA with its sequence complementary to a region of the template just upstream from the insert is annealed to the template to serve as a primer for the synthesis. In the presence of the four natural deoxyribonucleoside triphosphates (dNTP's), a DNA polymerase will extend the primer from the 3'-end to produce a complementary copy of the template in the region of the insert. To produce a complete set of sequencing fragments, four reactions are run in parallel, each containing the four dNTP's along with a single dideoxyribonucleoside triphosphate (ddNTP) terminator, one for each base. ($^{32}P$-Labeled or fluorophore-labelled dNTP is added to afford labeled fragments.) If a dNTP is incorporated by the polymerase, chain extension can continue. If the corresponding ddNTP is selected, the chain is terminated. The ratio of ddNTP to dNTP's is adjusted to generate DNA fragments of appropriate lengths. Each of the four reaction mixtures will, thus, contain a distribution of fragments with the sane dideoxynucleoside residue at the 3'-terminus and a primer-defined 5'-terminus.

In both the Sanger and Maxam-Gilbert methods, base sequence information which generally cannot be directly determined by physical methods has been converted into chain-length information which can be determined. This determination can be accomplished through electrophoretic separation. Under denaturing conditions (high temperature, urea present, etc.), short DNA fragments migrate as if they were stiff rods. If a gel matrix is employed for the electrophoresis, the DNA fragments will be sorted by size. The single-base resolution required for sequencing can usually be obtained for DNA fragments containing up to several hundred bases.

To determine a full sequence, the four sets of fragments produced by either Maxam-Gilbert or Sanger methodology are subjected to electrophoresis. This results in the fragments being spatially resolved along the length of the gel. One method of discriminating the dyes (which replace the $^{32}P$ label) and using this information to determine DNA sequences is described in the Prober et. al. application. This system is available in a commercial instrument known as the Genesis™ 2000 available from E. I. du Pont de Nemours and Company, Wilmington, Dela. The Genesis™ system for sequencing DNA, comprising a means for detecting the presence of radiant energy from closely-related yet distinguishable reporters or labels, which are covalently attached to compounds which function as chain terminating nucleotides in a modified Sanger DNA chain elongation method. Distinguishable fluorescent reporters are attached to each of the four dideoxynucleotide bases represented in Sanger DNA sequencing reactions, i.e., dideoxynucleotides of adenine, guanine, cytosine, and thymine. These reporter-labeled chain terminating reagents are substituted for unlabeled chain terminators in the traditional Sanger method and are combined in reactions with the corresponding deoxynucleotides, an appropriate primer, template, and polymerase. The resulting mixture contains DNA fragments of varying length that differ from each other by one base which terminate on the 3' end with uniquely labeled chain terminators corresponding to one of the four DNA bases. This new labelling method allows elimination of the customary radioactive label contained in one of the deoxynucleotides of the traditional Sanger method.

Detection of these reporter labels can be accomplished with two stationary photomultiplier tubes (PMT's) which receive differing wavelength bands of fluorescent emissions from laser-stimulated reporters attached to chain terminators on DNA fragments. These fragments can be electrophoretically separated in space and/or time to move along an axis perpendicular to the sensing area of the PMT's. The fluorescent emissions first pass through a dichroic or other wavelength selective filter or filters, placed so as to direct one characteristic wavelength to one PMT, and the other characteristic wavelength to the other PMT. In this manner, different digital signals are created in each PMT that can be ratioed to produce a third signal that is unique to a given fluorescent reporter, even if a series of fluorescent reporters have closely spaced emission wavelengths. This system is capable of detecting reporters which are all efficiently excited by a single laser line, such as 488 nm, and which have closely spaced emissions whose maxima usually are different from each other by only 5 to 7 nm. Therefore, the sequential base assignments in a DNA strand of interest can be made on the basis of the unique ratio derived for each of the four reporter-labeled chain terminators which correspond to each of the four bases in DNA.

While the base information is contained in fluorescent labels in the Genesis™ 2000 unit, it is noted that the information could also be contained in a colorimetric label (S. Beck, *Anal. Biochem.* 164 (2) 514–520 (1987)), chemiluminescent (S. Beck, *Nucleic Acids Res.* 17 5115–5123 (1989)) or other signal.

The Genesis™ DNA sequencer is designed to take advantage of the dideoxy chain termination chemistry. In order to employ this chemistry, it was necessary to use four chemically-similar dyes to distinguish the four bases A, C, G, and T. Unless the dyes are carefully chosen and exhaustively evaluated, their electrophoretic mobility may differ in some DNA sequences, leading to a scrambling of sequence information. The four dyes, chosen for similar electrophoretic mobility, had overlapping emission and excitation spectra. The need to distinguish these dyes without the excessive light loss of extremely narrow-band filters led to a two-channel detection scheme, in which the ratio of two signals is used to determine which base has passed the detector. When peaks are well-resolved and noise-free, the ratiometric signals are easy to interpret (FIG. 1). However, to maximize the amount of sequence information that can be obtained from each run, it is necessary to accurately interpret the two-channel signal under conditions of poor peak resolution and significant noise.

The methods for analysis of two-channel data under these conditions differ from those used to process conventional electrophoretograms and chromatograms. The output of the analysis described here is a sequence of base identifications, A, C, G, or T, while in chromatography, the desired output is typically a list of peak positions and areas. Chromatographic processes generally do not involve two detector signals coupled by one of four ratios. This relationship between the two signals is a special property of the sequencer described in the Prober et al. patent application. Computational efficiency is a more important consideration for sequencing than for chromatography. In chromatography, useful results can be obtained by performing extensive computations on two or three peaks; in sequencing, it may be necessary to analyze 300 to 600 peaks.

The ratiometric scheme of Prober et al also presents a signal interpretation problem different from that of other DNA sequencers. Sequencers employing primer chemistry are described in [L. M. Smith et al. *Nucleic Acids Res.* 13 2399–2412 (1985) and W. Ansorge et al. *J. Biochem. Biophys. Meth.* 13 315–323 (1986)]. These sequencers employ four signal channels, one for each base. Other sequencers, such as that described by Kambara et al. [H. Kambara et al., *Biotechnology* 6 816–821 (1988)], employ one signal in each of four electrophoresis lanes. These systems employ yet another class of data analysis methods, since the results from four separate lanes must be registered, or aligned, in the proper time sequence.

In these automated versions of DNA sequencing the reporter may be fluorimetric as is described in the Prober et al. application, colorimetric (S. Beck, *Anal. Biochem.* 164 (2) 514–520 (1987), chemiluminescent (S. Beck, *Nucleic Acids Res.* 17 5115–5123 (1989), or of some other type.

Sequencers employing primer chemistry such as (Hunkapiller et al., U.S. Pat. No. 4,811,218) are not so restricted in the selection of dyes that may be used to tag the DNA fragments. These sequencers can employ four signal channels, one for each base, and thus do not require the complex algorithms needed to interpret ratiometric signals. On the other hand, these sequencers cannot enjoy the advantages of terminator chemistry. In particular, primer chemistry requires four separate reaction tubes for each sample to be sequenced, while terminator chemistry requires only one. In addition, primer chemistry is susceptible to errors from "false stops", erroneous signals produced when a polymerass is unable to proceed past a certain point on a DNA strand.

Other sequencers, such as that described by Kambara et al. (H. Kambara et al., *Biotechnology* 6 816–821 (1988), employ one signal in each of four electrophoresis lanes. This overcomes many of the difficulties encountered with the resolution problem of the prior art automated DNA sequencers. These systems employ yet another class of data analysis methods, since the results from four separate lanes must be registered, or aligned, in the proper time sequence. Once the lanes are registered, the data analysis methods for these sequences can be identical to those of Hunkapiller et al. Proper registration for the lanes is obviously crucial to correct sequence determination. If lanes are improperly registered, the corresponding bases are interpreted out of order. The problem of registration of four lanes is complex because it is combinatorial in nature. For a given pair of closely spaced bands in all four lanes, there are 4!=2×3×4=24 possible orderings of the bands. Only one corresponds to the correct sequence. The registration process can introduce errors in sequence interpretation, and therefore sequencers of the type described by Kambara may produce a smaller amount of accurate sequence information than those of Hunkapiller, given equal resolution and signal-to-noise ratio. Note also that these sequences require not only four reaction tubes, but also four electrophoresis lanes for each DNA sample to be analyzed.

SUMMARY OF THE INVENTION

These twin problems of accuracy or resolution and registration are largely overcome by the method of the present invention. According to the method of this invention the sequence of bases may be determined, i.e., "called", by using two electrophoresis lanes for each sample whose DNA is to be sequenced. Each lane incorporates two terminator dyes. According to the invention a method for sequencing DNA to ascertain the sequence of the four bases G,C,A and T comprises the steps of: producing a first set of DNA fragments having reporter labeled terminators for two of the four bases, each base having a different reporter, producing a second set of DNA fragments having reporter labeled terminators for the remaining two of the four bases, each base having a different reporter, separating the respective first and second sets by gel electrophoresis, generating a first signal for each of the respective sets that varies in amplitude to form peaks in accordance with a characteristic of the reporter and the rate at which a base moves through the gel, generating a second signal for each of the respective sets that varies in amplitude to form peaks in accordance with a characteristic of the reporter and the rate at which each has moved through the gel, and converting the first and second signals to signals corresponding to the four bases in the order of their movement through the gel.

In a preferred embodiment of the invention the first set of DNA fragments includes G and C. This tends to overcome the well-known G-C compression phenomenon in which the spacing between G signal peaks and immediately subsequent signal peaks is highly variable. Further, in accordance with the preferred embodiment of this invention, the first and second sets are separated in adjacent lanes on the gel. This is advantageous since the DNA fragments to be separated are subjected to essentially the same gel composition, thermal environment, and electric field. During sequencing, the four base signals are ordered according to their rate of passage through the gel. Also the reporters used as the first set may be the same as those used for the second set.

This method has many advantages. Terminator chemistry may be used without the complexity of ratiometric signal processing as described by Prober et al. The method requires the use of only two reporters with similar electrophoretic mobility and different spectral characteristics, rather than the four reporters required by a single-lane system. Lane registration is involved, but it is not combinatorial in nature, since there are only two possible orderings of two objects. The two signals can simply be "slid" with respect to each other, until proper alignments determined, as described below. Because neither ratios nor complex registration algorithms are employed, this method is capable of producing a larger quantity of accurate sequence information from a given sample than the prior art methods. The use of two lanes rather than four is more economical than alternative four-lane methods for obtaining four separate signals.

In still another alternative method, the invention may be used with primer labelling. Either Sanger or Maxim-Gilbert chemistry may be employed.

BRIEF DESCRIPTION OF THE DRAWINGS

The invention may be more easily understood by considering the following drawings in connection with the description in which.

DETAILED DESCRIPTION OF THE PREFERRED EMBODIMENT

Figure 1:
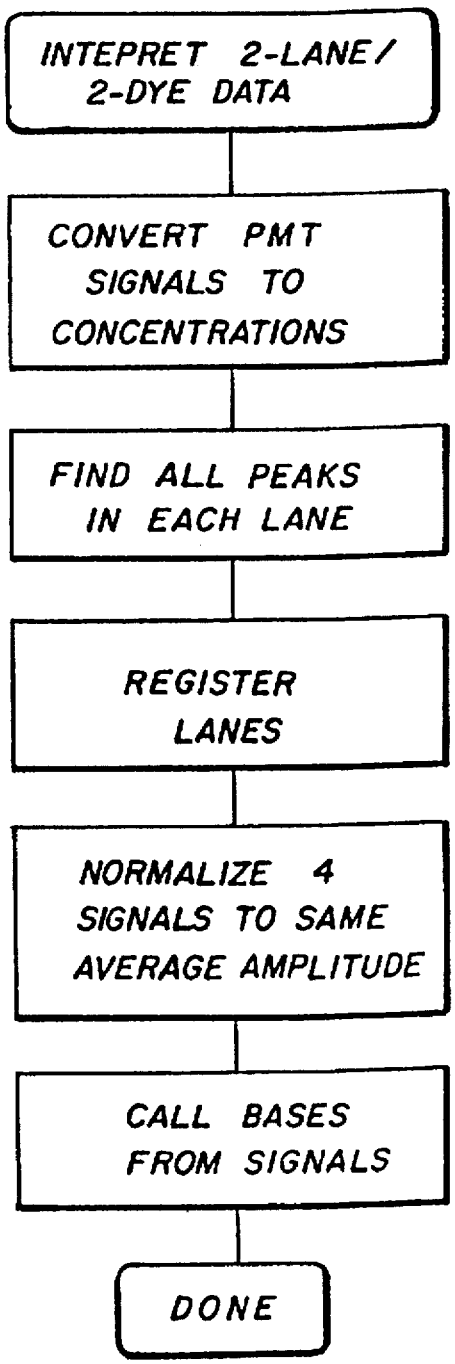
FIG. 1 is a flowchart depicting the steps according to the method of this invention for sequencing DNA fragments.

The method Of this invention will be described in connection with the Genesis™ 2000 Sequencer which has two detectors that provide the output signals of R and T as described above. These output signals vary in amplitude to form peaks in accordance with the characteristic of the reporter used with the DNA fragments and the time at which a base moves through the gel. Using the reagent kits available for use with the Genesis™ 2000 Sequencer, for example, DNA samples are prepared and two terminator reactions are carried out with fluorescent dideoxy terminators. In one reaction, only two terminators, G and C, are included. In the other reaction, only the A and T terminators are included. This pairing is preferred because of the G-C compression phenomenon; the spacing between G signal peaks and immediately subsequent C signal peaks is highly variable. If the G and C terminators are included in an single reaction, it will not be necessary later for the algorithm which aligns the two lanes to take G-C spacing variability into account. The two reaction mixtures are separated on a sequencing gel. It is preferable to place the two mixtures in adjacent lanes on the gel, to minimize the misalignment between the two lanes. From each lane, two photomultiplier signals are derived using the Genesis apparatus.

The preferred combination of dyes and terminators is G-dye 1, A-dye 1, C-dye 2, and T-dye 2. Many potential choices for dye 1 and dye 2 may be available. Dye 1 and dye 2 should be chosen so that there is adequate spectral separation to distinguish between them, and so that the strongest and most evenly-distributed signals for all four bases are obtained. This latter parameter must be determined experimentally, since it depends in a complicated way on the enzyme and reaction conditions being employed for sequencing.

The four signals (two photomultiplier signals from each of two lanes) must be converted to signals corresponding to the four bases in the correct order. First, each pair of photomultiplier signals must be converted to an orthogonal basis so that one signal corresponds to one base, and the other signal corresponds to the other base. This can be done based on the fact that the two photomultipliers will respond differently to the two bases, using the G-C lane as an example:

$$P_1 = \beta_{G1} \cdot G + \beta_{C1} \cdot C$$

$$P_2 = \beta_{G2} \cdot G + \beta_{C2} \cdot C$$

where $P_1$ and $P_2$ are the PMT signals, G and C are the actual concentrations of dye being sensed when the signals are obtained, and the $\beta$'s describe the response of the two PMT's to the two dyes. It is then possible to derive signals representing the concentrations of the dyes being sensed:

$$G = \beta_{C2} \cdot P_1 - \beta_{C1} \cdot P_2)/(\beta_{C2}\beta_{G1} - \beta_{C1}\beta_{G2}) \quad [1]$$

$$C = \beta_{G2} \cdot P_1 - \beta_{G1} \cdot P_2)/(\beta_{G2}\beta_{C1} - \beta_{G1}\beta_{C2}) \quad [2]$$

From the other lane, A and T signals can be derived identically.

Next it is necessary to register or align the G-C and A-T signals. There are many algorithms known for registration of signals, i.e., A. Rosenfeld, et al., *Digital Picture Processing*, Academic Press, 297–302 (1976). One particular method is described in the example below. Once the signals are ordered, the data is identical in appearance to that produced by the system of U.S. Pat. No. 4,811,218 issued to Hunkapiller et al. in which each signal corresponds to one base. Any means of sequence interpretation applicable to that data may be used.

Figure 2:
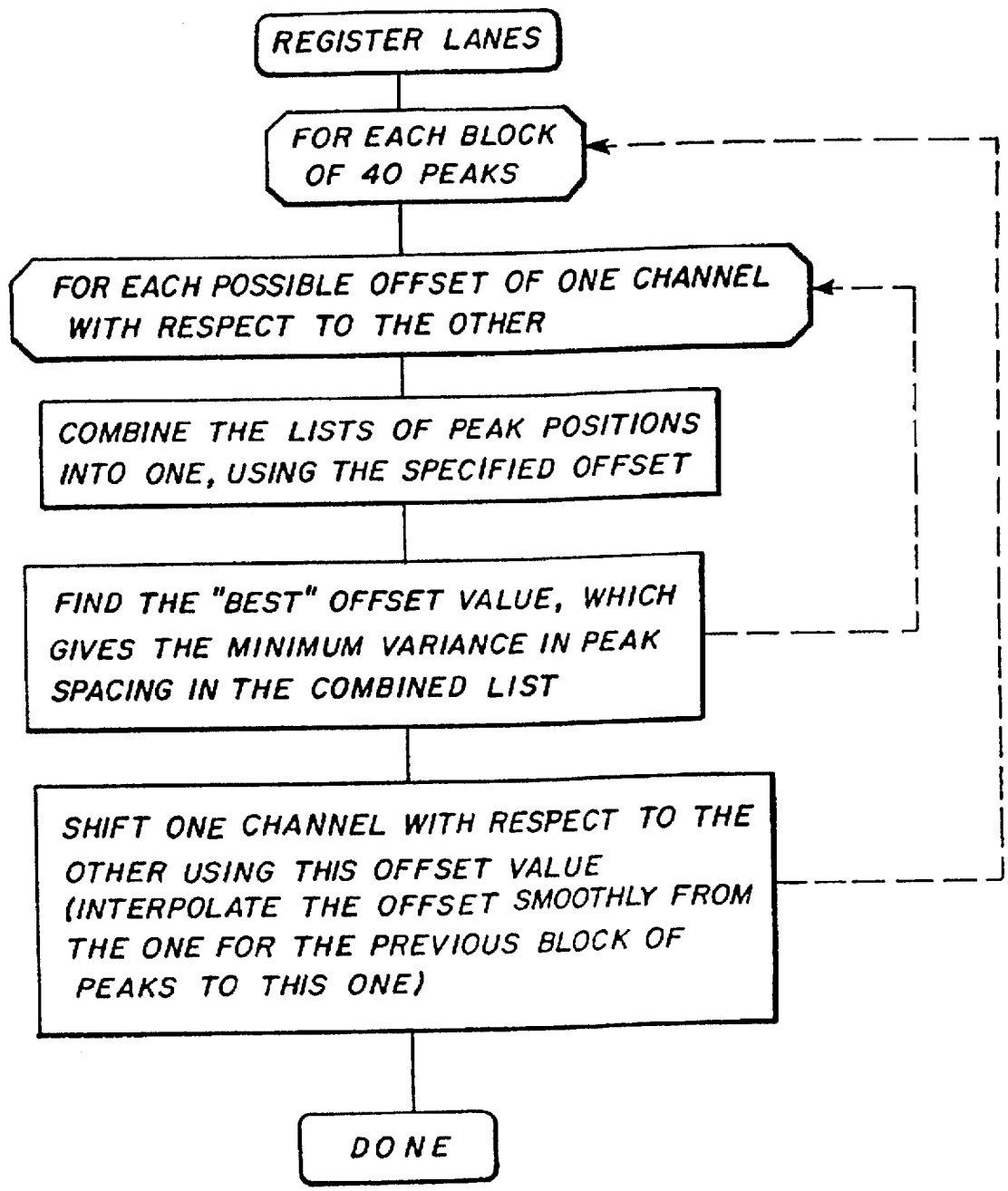
FIG. 2 is a flowchart depicting the steps used in the method for registering the lanes as shown in FIG. 1.

As shown in the flowchart of FIG. 1, registration of the lanes is accomplished by the procedure set forth in greater detail in the flowchart of FIG. 2. The four signals used as input to the two-lane data analysis process correspond to the photomultiplier signals in the G-C and A-T lanes. These four photomultiplier signals are converted into four base signals A,G,C and T using the equations 1 and 2 above. Next the peaks in the G-C lane are located. First, the G and C signals are summed. The resulting data array is scanned from beginning to end, and any point at which the first derivative of the data crossed zero with a slope exceeding a certain threshold (0.00015 V/data point) is taken to be a peak location. Thus a list of peaks in the G-C channis is obtained.

A list of peaks in the A-T channel is obtained from the other lane data by an identical process.

Figure 3:
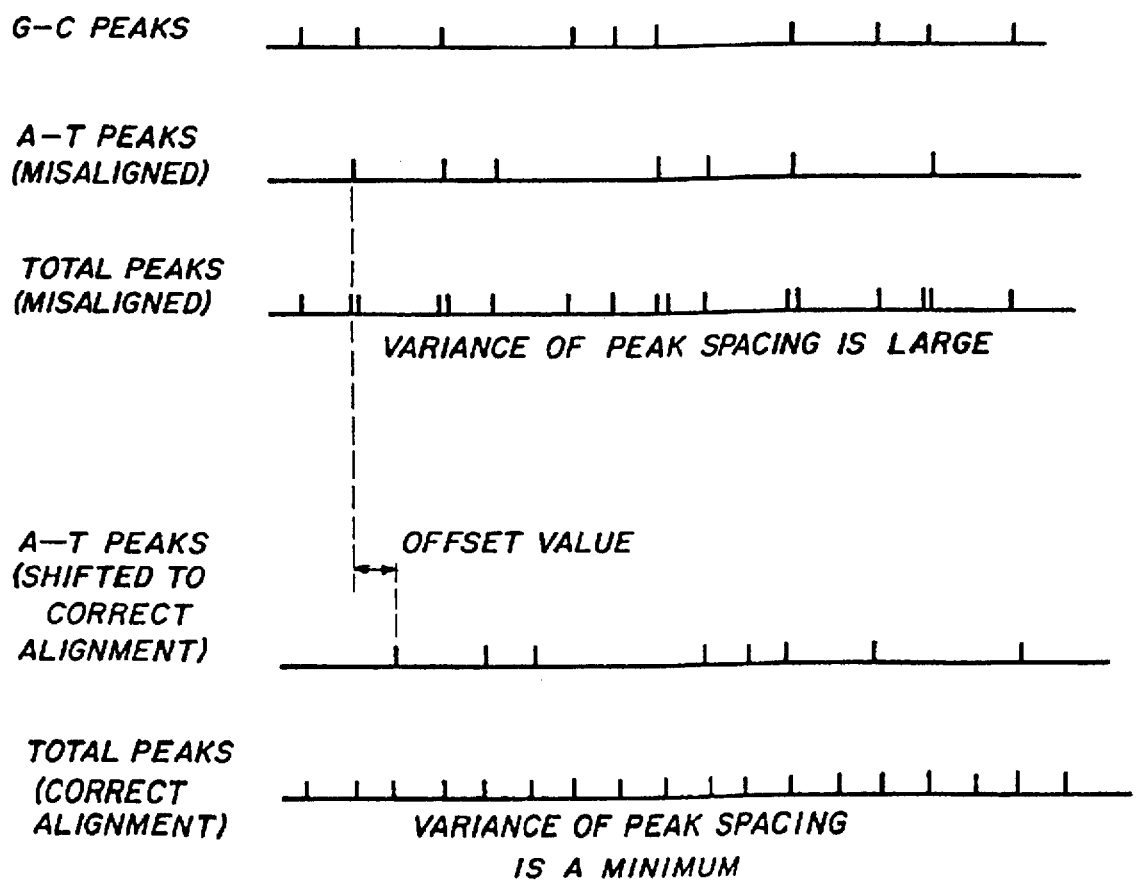
FIG. 3 are plots of the detected peaks plotted against time depicting the manner in which the peaks' spacing is set in order to properly space the several peaks.

Next the alignment of the two arrays is determined. The alignment is carried out on groups of 40 peaks. As shown in FIGS. 2 and 3, when the two lists of peak positions are combined with improper alignment, there is a wide variance in the spacing between peaks in the combined list. When the A-T peaks are shifted by an offset value, that places them in their proper positions, the spacing variance is reduced. The A-T peak positions are shifted with respect to the G-C peak positions until a degree of offset is found that results in a minimum variance in peak-to-peak spacing when the G-C and A-T peak lists are combined. Using the offsets so determined, a new A-T data array is created and aligned to the G-C data array. Since the offset varied from one 40-peak block to the next, a linearly interpolated offset value is used at each data point.

In order to facilitate peak calling, data is normalized, that is, the arrays are scaled to give identical average signal amplitudes in all four channels.

Figure 4:
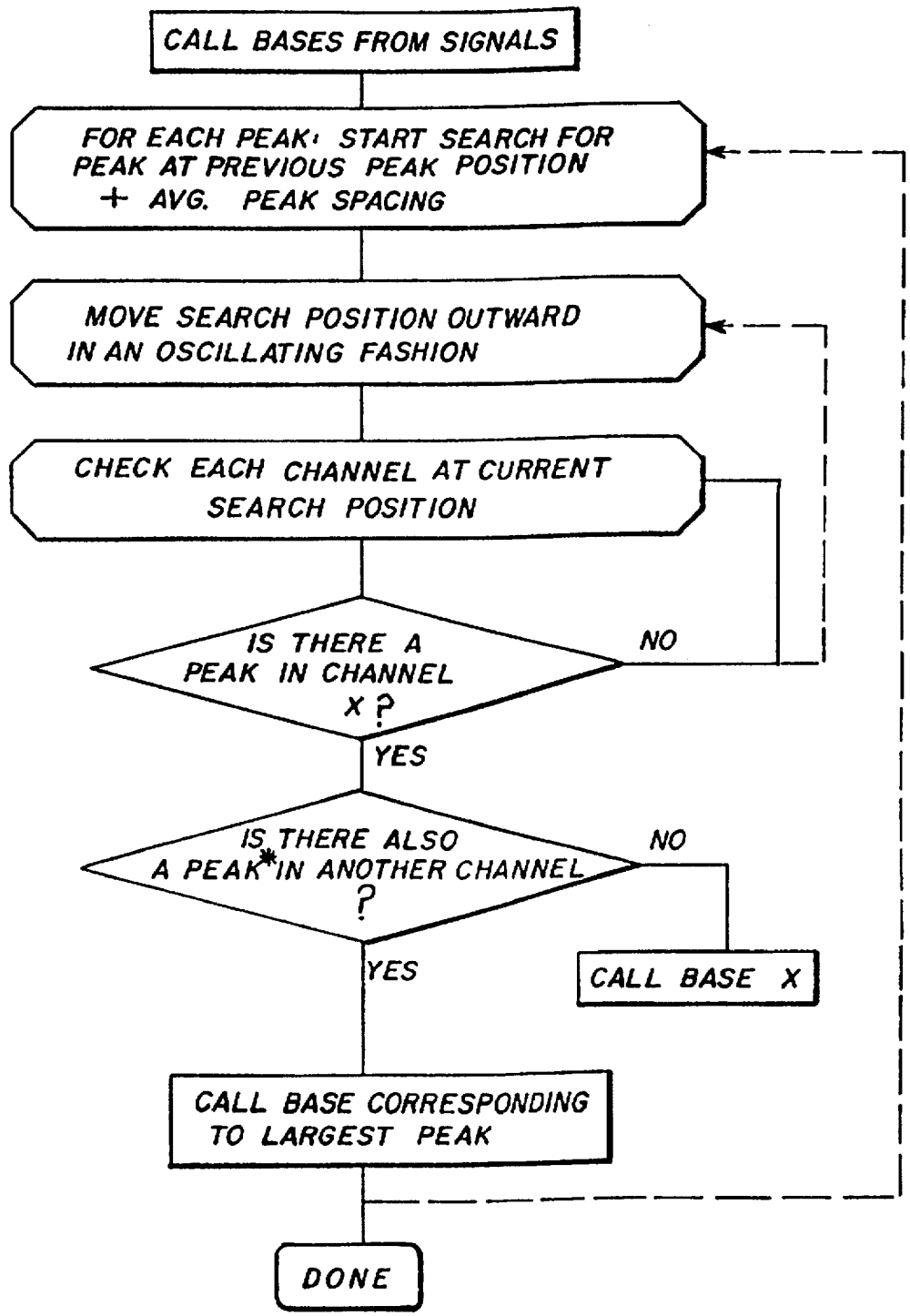
FIG. 4 is a flowchart depicting the details of the base calling step of the flowchart of FIG. 1.

Base calling begins with the first peak in any of the four arrays, and proceeds down the arrays, one peak at a time. Once an expected peak position is determined as shown in the flowchart of FIG. 4, an oscillating search is performed about this position until a peak is found. A peak is defined by the zero-crossing criterion described above. If only one of the four channels, A, C, G, or T, has a peak at that position, the corresponding base is called. If two channels have a peak in the same place (due usually to noise in one of the channels), the base corresponding to the largest peak is called.

Alternatively, this invention employing two lanes and two dyes can be used with primer labelling. In this case, either Sanger or Maxam-Gilbert chemistry may be employed. When the invention is employed in this fashion, four reactions, as is the case for primer labelling, rather than two must be performed. However, these four reactions can be combined to require only two lanes on the gel, e.g., the G and C pots and the A and T pots may be combined. Thus the efficient use of gel space and the simplification in lane registration can still be exploited, even though primer chemistry is being used.

The method of this invention produces more accurate and greater number of bases called than has heretofore been possible.

EXAMPLE

The following example illustrates the principle of two-lane, two-dye sequencing. In actuality, four dye-terminators were used: ddG-SF505, ddA-SF512, ddC-SF519, and ddT-SF526. This permitted the use of commercially-available labelled terminator reagents from the Genesis System. A true two-dye system could utilize dye-terminator combinations whose synthesis is described in Prober et al. application, for example, ddG-SF505, ddA-SF505, ddC-SF519, and ddT-SF519 which are those that are available commercially in the Genesis™ 1000 kits. The samples in this example were run and analyzed in pairs, in a way that did not involve distinguishing the G dye from the A dye, or the C dye from the T dye. It should therefore be apparent that the substitution of SF505 for SF512, and of SF-519 for SF-526, does not materially affect the results.

All reagents were commercial products of the Biotechnology Systems Division, E. I. du Pont de Nemours and Company, Wilmington, Dela., except as noted. Three micrograms of M13mp18 template DNA were used for each of three reactions, a G-C reaction, an A-T reaction, and a control. Each reaction mixture was incubated with 15 ng of 17-mer universal M13 primer oligonucleotide (5'-GTTTTCCCAGTCACGAC-3') (SEQ ID NO:1) in Sequenase™ buffer (U.S. Biochemical Corp., Cleveland, Ohio) a volume of 21 μL at 95° C. for 2 minutes to denature the template, and then at 37° C. for 10 minutes to anneal the primer. The G-C reaction tube then received 2.5 μL dithiothreitol, 3.0 μL of 75 μM each of dATP, dCTP, dGTP, and dTTP, and 0.5 μL of a mix of 1.12 μM ddGTP-F fluorescent labeled G terminator, and 8.96 μM ddCTP-F fluorescent labeled C terminator. The A-T reaction tube then received 2.5 μL dithiothreitol, 3.0 μL of 75 μM each of dATP, dCTP, dGTP, and dTTP, and 0.5 μL of a mix of 3.36 μM ddATP-F fluorescent labeled A terminator, and 112 μM ddTTP-F fluorescent labeled T terminator. The control reaction received all four terminators. Each reaction received 0.5 μL of Sequenace™ T7 polymerase (U.S. Biochemical Corp., Cleveland, Ohio), and was incubated at 42° C. for 2 min. An additional 1.0 μL of Sequenase™ was added to each, and incubated for another 5 min at 42° C. Unincorporated ddNTP-F was removed from each reaction with a Sephadex G-50 Spin Column.

The G-C, A-T, and control reaction mixtures were then loaded in adjacent lanes and electrophoresed on a Genesis™ 2000 DNA Analysis System (E. I. du Pont de Nemours and Company, Wilmington, Dela.) at 18W using a 6% polyacrylamide gel (19:1 crosslinking). Data were collected for 10 hours and analyzed on a Macintosh II computer (Apple Corp., Cupertino, Calif.) using the program shown in FIG. 1, and flowcharted in FIG. 2.

The data analyzed by this method yielded 501 bases of sequence information at 97% accuracy, with 3 ambiguous calls (no peak located within the expected peak interval). The control reaction was analyzed using software supplied with the Genesis™ 2000 DNA Analysis System (Version 3.0.2), and produced 379 bases at 97% accuracy, with 23 ambiguous calls. Thus a greater amount of information was obtained from the template utilizing the two-lane, two-dye method.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:

( A ) LENGTH: 17 base pairs

```
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

GTTTCCCAG TCACGAC                                                      1 7
```

What is claimed is:

1. A method for sequencing DNA to ascertain the sequence of the four bases G, C, A, and T comprising the steps of:
   1) producing a first set of reporter labelled DNA fragments for two of the four bases, each base having a different reporter;
   2) producing a second set of reporter labelled DNA fragments for the remaining two of the four bases, each base having a different reporter;
   3) separating the respective first and second sets by gel electrophoresis;
   4) generating a first signal for each of the respective sets that varies in amplitude to form peaks in accordance with a characteristic of the reporter and the rate at which the labelled base moves through the gel;
   5) generating a second signal for each of the respective sets that varies in amplitude to form peaks in accordance with a characteristic of the reporter and the rate at which the labelled base moves through the gel;
   6) dividing each of the first and second sets into corresponding blocks of bases;
   7) selecting the amount of shift between the corresponding blocks of the first and second sets which minimizes peak to peak variance, and;
   8) interpolating the shifts between the corresponding blocks of the first and second sets to align the first and second sets into a single set of four signals corresponding to the four bases in the order of their movement through the gel.

2. A method according to claim 1 in which the first set of DNA fragments is G and C.

3. A method according to claim 1 in which the first and second sets are separated in adjacent lanes on the gel.

4. A method according to claim 2 in which the first and second sets are separated in adjacent lanes on the gel.

5. A method of claim 4 wherein the reporters used for the first set are the same as used for the second set.

6. A method according to claim 5 in which the first set of DNA fragments is G and C.

7. A method according to claim 3 in which the first and second sets are separated in adjacent lanes on the gel.

8. A method according to claim 1 wherein the DNA fragments have terminators which are labelled.

9. A method according to claim 1 wherein the DNA fragments have primers which are labelled.

* * * * *